United States Patent [19]

Bussiere et al.

[11] 4,450,139

[45] May 22, 1984

[54] LIGHT GENERATING APPARATUS FOR CURING DENTAL RESTORATIVE COMPOSITES

[75] Inventors: Ronald L. Bussiere, Edmonds; Robert J. Smith, Lynnwood, both of Wash.

[73] Assignee: Solid State Systems, Corporation, Lynnwood, Wash.

[21] Appl. No.: 374,517

[22] Filed: May 3, 1982

[51] Int. Cl.$^3$ .............................. B01J 1/10; B01J 1/12
[52] U.S. Cl. ............................. 422/186.3; 204/159.11; 250/504 R; 250/504 H; 315/360; 362/804
[58] Field of Search ............... 204/159.11; 250/504 R, 250/504 H; 315/241 R, 326, 360; 362/32, 263, 293, 804; 422/186.3

[56] References Cited

U.S. PATENT DOCUMENTS

| | | | |
|---|---|---|---|
| 3,712,984 | 1/1973 | Lienhard | 362/32 X |
| 3,868,513 | 2/1975 | Gonser | 362/32 X |
| 3,970,856 | 7/1976 | Mahaffey et al. | 250/504 H |
| 3,978,341 | 8/1976 | Hoell | 315/241 R |
| 4,229,658 | 10/1980 | Gosner | 250/504 H |
| 4,309,617 | 1/1982 | Long | 250/504 H |

FOREIGN PATENT DOCUMENTS

| | | | |
|---|---|---|---|
| 2136694 | 2/1973 | Fed. Rep. of Germany | 250/504 |
| 2070900 | 9/1981 | United Kingdom | 422/186.30 |

Primary Examiner—Leland A. Sebastian
Attorney, Agent, or Firm—Christensen, O'Connor, Johnson & Kindness

[57] ABSTRACT

An apparatus for photochemically curing organic composites used to repair teeth includes a quartz halogen lamp (12) which is activated for a particular length of time by a cycle control circuit (42) which produces a control signal for a preselected time interval. A switching circuit (38) is coupled with the cycle control circuit (42) to interconnect an alternating current source with the quartz halogen lamp (12) at a point in the alternating current cycle when the alternating current crosses a zero voltage level. The control circuit (42) is operably coupled to a time delay circuit (40) which activates the control circuit (42) after a preselected time period after activation of the control circuit (40).

22 Claims, 3 Drawing Figures

LIGHT GENERATING APPARATUS FOR CURING DENTAL RESTORATIVE COMPOSITES

DESCRIPTION

1. Technical Field

The present invention relates to an apparatus capable of producing light for a selectively adjustable length of time, and more particularly to an apparatus for generating light to cure organic composites used to fill or repair teeth.

2. Background Art

In the past, dentists primarily used gold and silver alloys to fill or otherwise repair teeth. Other lesser expensive restorative materials are now being used as substitutes for gold and silver. The newer materials also have the advantages that they match the color of a patient's teeth and also are highly durable. Typically the newer materials are composites composed of an organic bonding agent and an inorganic filler material. The composite material is applied to the patient's tooth in thin layers and then cured by directing light at the material.

Known apparatus for curing dental repair composites typically include a light bulb disposed within a housing and a switch for interconnecting the light bulb with standard alternating current from a wall socket. A flexible cord composed of fiber optic strands directs the light from the bulb to the patient's tooth. A filter might be utilized to attenuate frequencies of light known to be harmful, such as the near infrared frequencies.

A drawback of known curing light producing apparatus is that the bulb tends to burn out in a relatively short period of time. Not only are the bulbs expensive, but they are often difficult to replace.

A further disadvantage of known curing light generating units is that they are cumbersome to operate in that after properly positioning the tip of the fiber optic cord, the dentist must then reach over to the housing to turn the unit on. If the housing is located too far from the patient, an assistant or other person must be called in to activate the unit.

It is a primary object of the present invention to overcome the shortcomings of known curing light generating systems by providing an apparatus which is capable of producing a high intensity light to cure the composite material utilized to repair teeth which includes a long lasting, readily replaceable bulb and which initiates the curing light after the expiration of a dwell time interval beginning when the unit is initially activated thereby giving the dentist adequate time to properly position the tip of a light cord.

DISCLOSURE OF THE INVENTION

The present invention relates to an apparatus for generating high intensity light for a preselected period of time to cure organic composite materials used to fill or otherwise restore teeth. To this end, the light generating apparatus includes a halogen lamp which is nominally maintained at a low intensity level through a transformer which reduces the voltage of a standard alternating current supply to approximately three and one-half volts. To cure composite material, the transformer is switched to a high output voltage state to thereby fully energize the lamp. The light from the lamp is transmitted to a patient's tooth through a flexible light cord composed of fiber optic strands. A contra angle probe is mounted on a handle attached to the free end of the light cord to enable the operator to accurately direct the light to the desired location in the patient's mouth. A filter may be positioned adjacent the lamp or in the probe to block unwanted light, such as frequencies in the near infrared or the higher ultraviolet range which have been found to be harmful to gum tissue.

For optimum curing of the composite material, the length of time that the curing light is directed at the material must be regulated. To this end, the present invention utilizes a cycle control circuit which energizes the lamp for a selected period of time, for instance, from ten to sixty seconds in ten-second increments. The particular cycle length may be manually preset by the operator through a time select switch.

The high intensity light cycle is initiated by the closing of an operating cycle start switch. Once the cycle start switch has been activated, to give the operator sufficient time in which to position the probe at the end of the light cord, the present invention utilizes a time-delay or dwell circuit. The circuit delays the activation of the cycle control circuit until after an adjustable time interval has transpired from the time that the cycle start switch was actuated. The dwell circuit includes an integrated monolithic timing circuit which is adapted to operate as a time delay unit by an external resistor and capacitor.

According to another aspect of the present invention, the precise time at which the lamp is switched to its higher operating level relative to the phase of the alternating current supply is controlled by a switching circuit which is activated by the operating cycle control circuit. The switching circuitry is designed to maintain the lamp at its low intensity level until the alternating current power supply crosses through a zero voltage point in its cycle, whereupon the switching circuit switches the transformer to its high output voltage level. Switching the transformer when the alternating current power source is at zero volts enables the current flowing through the lamp to gradually increase, rather than instantaneously imposing the full output of the transformer across the lamp filament. This eliminates cold filament inrush and flash-overcurrent that could otherwise damage the lamp.

In a further aspect of the present invention, an audible signal is produced at the time the lamp is switched to its fully energized state and then once every ten seconds during the duration of the operating cycle to inform the operator of what portion of the operating cycle has already elapsed. The audible signal is produced by a tone generating circuit which energizes a piezoelectric transducer. The tone generating circuit is in turn activated by the operating cycle control circuit.

To ensure that the curing light is supplied for precisely the desired time interval, a highly regulated direct current (hereinafter "DC") signal is supplied to the operating cycle control circuitry, the time dwell circuitry and the tone generating circuitry. A diode rectifier bridge is coupled with a monolithic integrated circuit voltage regulator to convert the alternating current supply to a substantially uniform DC signal.

BRIEF DESCRIPTION OF THE DRAWINGS

The details of one typical embodiment of the present invention will be described in connection with the accompanying drawings, in which.

BEST MODE OF THE INVENTION

Figure 1:
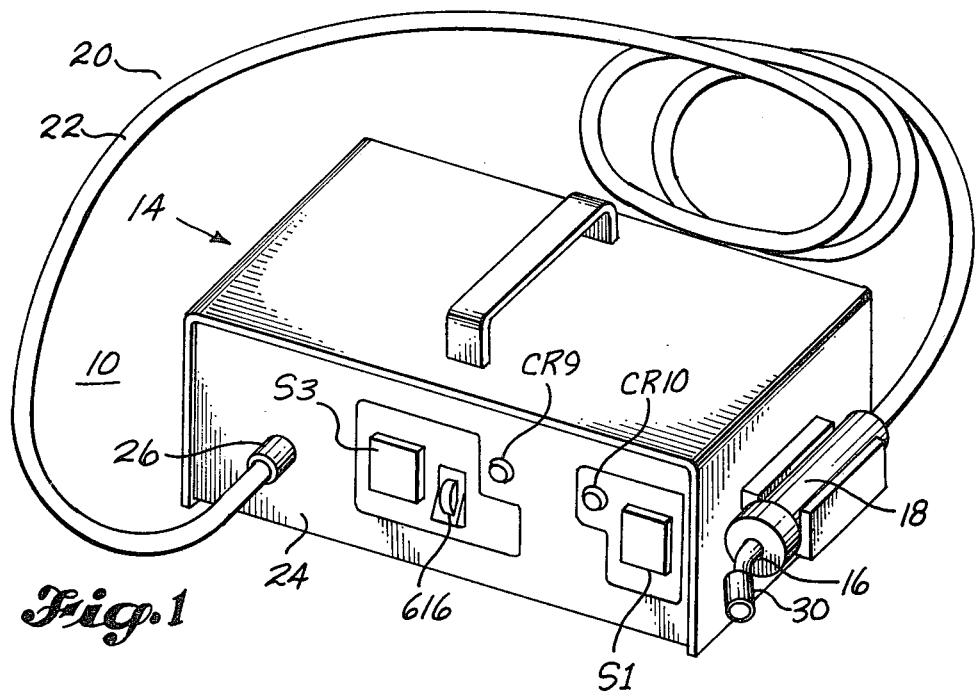
FIG. 1 is a pictorial view of the light generating apparatus of the present invention, specifically illustrating housing, light cord and probe.
Figure 2:
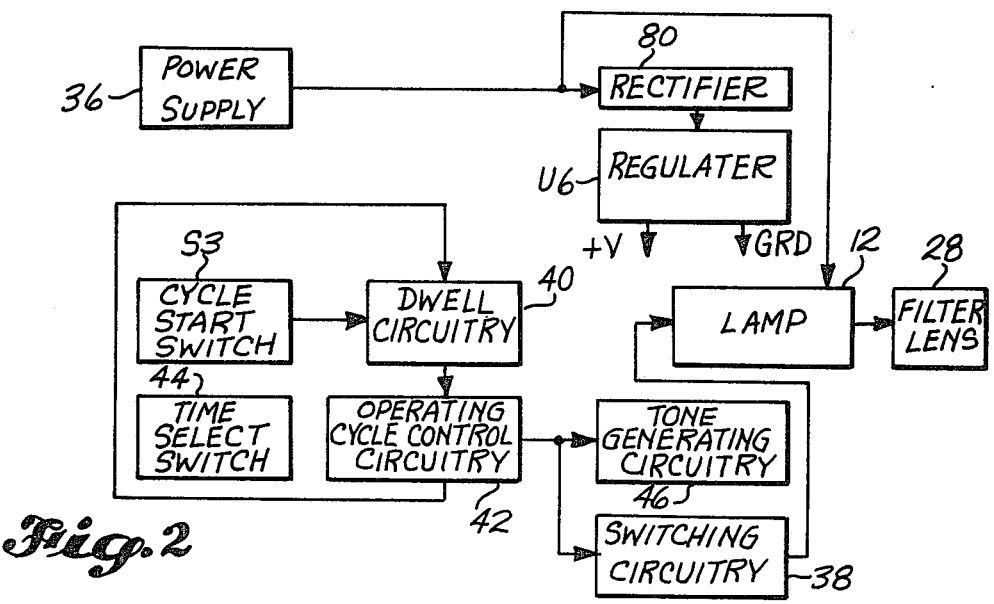
FIG. 2 is a block diagram of the light generating apparatus of the present invention.
Figure 3:
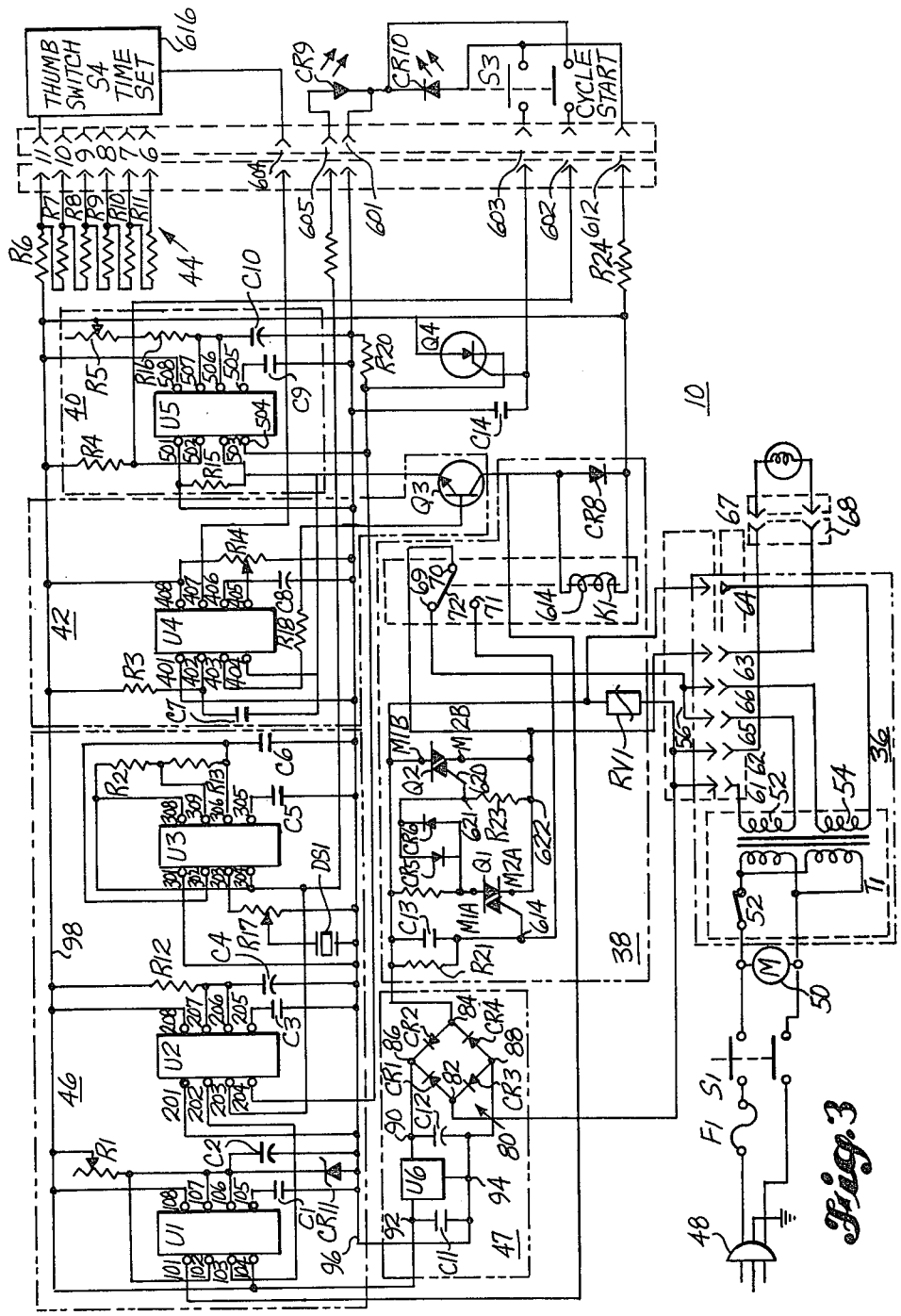
FIG. 3 is a circuit diagram of the light generating apparatus illustrated in block form in FIG. 2.

Referring initially to FIG. 3, a frequency regulated time duration controlled light generating apparatus 10 constructed according to the best mode of the invention currently known to applicant includes a lamp 12 which is capable of producing a high-level of light energy for curing organic composite material used by dentists to fill or otherwise repair teeth. Lamp 12 is located within a rectangularly-shaped housing 14, FIG. 1, which also houses the remainder of the electrical components of the present invention. Lamp 12 is preferably of a quartz halogen type; however, other types of lamps may be employed without departing from the scope of the present invention.

The light generated by lamp 12 is transmitted by a flexible light cord 20 to a contra angle probe 16 mounted on the end of a handle 18. Cord 20 is composed of a plurality of very small diameter fiber optic strands covered with an outer casing 22. The end of cord 20 opposite handle 18 is engaged within an opening provided in housing front panel 24 through the use of an appropriate fitting 26. The frequency range of the light emitted from probe 16 may be regulated by a filter (not shown) located, for instance, within housing 14 adjacent to lamp 12 or within probe 16 to attenuate harmful or otherwise unwanted light.

Referring specifically to FIG. 3, during the steady state or non-operating period, lamp 12 is energized by an alternating current (hereinafter "AC") power supply 36 at a low intensity or preheat level. During the operating cycle of the present invention, switching circuitry 38 is used to switch lamp 12 to a high intensity or operating level. The operating cycle is initiated by closure of a cycle start switch S3. This does not immediately shift lamp 12 to its operating level, but instead begins a delay or dwell time interval to give the operator adequate time to properly position probe 16 in the patient's mouth. To this end, closure of start switch S3 activates a dwell circuit 40 which at the end of a preset dwell or delay time interval transmits an output signal to an operating cycle control circuit 42. In response to the dwell circuit output signal, control circuit 42 produces a control signal for the length of time that it is desired to maintain lamp 12 at its operating level. The time duration of the control signal may be selectively varied by manually adjusting a time select switch 44. The control signal from circuit 42 is transmitted to switching circuit 38 to in turn switch lamp 12 to its operating level. Switching circuit 38 coordinates the timing of the switching of lamp 12 to its high intensity level with the voltage level of the AC power supply. Lamp 12 is switched to its high intensity state when the power supply is passing through a zero voltage level thereby gradually applying power to the lamp rather than possibly submitting the lamp to the maximum voltage produced by power supply 36.

The output signal produced by operating cycle control circuit 42 is also transmitted to a tone generating circuit 46 which produces an audible signal when the lamp 12 is initially fully energized and then periodically at fixed time periods during the remainder of the operating cycle. For instance, circuit 46 may be adjusted to produce the audible signal at ten-second intervals.

After the operating cycle expires, the control signal from circuit 42 terminates thereby causing switching circuit 38 to return lamp 12 to its low intensity state. Also, with the termination of the control signal, the tone generating circuit 46 is deactivated. Thereafter, a new operating cycle may be initiated by again closing cycle start switch S3, with the duration of the operating cycle preset by adjusting time select switch 44.

The electrical circuitry of the present invention will now be described in more detail in conjunction with the circuit diagram illustrated in FIG. 3. Light generating apparatus 10 includes an electrical plug 48 for interconnecting the apparatus with a standard AC service outlet, not shown. A switch S1 is provided to initiate power to apparatus 10. A fuse F1 is disposed between electrical plug 48 and switch S1 to protect apparatus 10 from high current levels. The closing of switch S1 activates a fan 50 which blows cooling air through housing 14 to help prevent overheating of the electrical components of the present invention.

Fan 50 is wired in parallel with a stepdown transformer T1 which produces a low-level output voltage of, for instance, three and one-half volts, across a first secondary winding 52. Transformer T1 produces a substantially larger output voltage of, for instance, fifteen volts, when first secondary winding 52 is connected in a series with a second secondary winding 54. The two secondary windings are connected together by a line 56 extending between connectors 65 and 66 of power supply 36. The non-joined end of first secondary winding 52 is connected to connector 61 while the corresponding end of second secondary winding 54 is connected to connector 64. Transformer T1 includes an internal thermally-activated switch S2 which automatically opens if the transformer approaches an overheated condition.

When S1 is closed, lamp 12 is nominally energized to a preheat or low intensity level by connecting the lamp across first secondary transformer winding 52. Connector 67 of lamp 12 is joined to connector 62 of power supply 36 which in turn is joined to connector 61. The opposite connector 68 of lamp 12 is joined to connector 63 of the power supply which in turn is joined to the opposite connector 65 of transformer secondary winding 52 through terminals 69 and 70 of a relay switch K1. Relay switch K1 is in its non-energized state when terminals 69 and 70 are interconnected by blade 72, as schematically illustrated in solid line in FIG. 3.

A DC signal source for operating dwell circuit 40, cycle control circuit 42 and tone generating circuit 46 is produced by rectifying the AC output of transformer T1. This is accomplished through the use of a DC power supply circuit 47 which includes a rectifier bridge 80 composed of four rectifier diodes CR1, CR2, CR3, and CR4 arranged in a well-known manner. Bridge 80 is subjected to the full output of transformer T1 by interconnection of connector 61 of power supply circuit 36 with terminal 82 of the bridge and interconnection of connector 64 of the power supply circuit with bridge terminal 84.

A DC signal is outputted at pin 86 and a reference or ground signal is produced at terminal 88 of the rectifier bridge. Although the output from terminal 86 of bridge 80 is essentially a DC signal, its level varies in response to changes in the output voltage from transformer T1 and from current surges occurring, for instance, when lamp 12 is switched from its low intensity to high intensity level. To provide a substantially constant DC signal for precise operation of the present invention, the output voltage from rectifier bridge 80 is regulated by an integrated circuit voltage regulator U6 having an input pin 90 receiving the DC signal from the rectifier bridge. Regulator U6 constantly compares the voltage of the DC signal which it outputs at pin 92 with ground at pin 94 so that the output voltage remains essentially constant, for instance at twelve volts.

DC supply circuit 47 includes a capacitor C12 connected across output terminal 88 and ground terminal 88 of rectifier bridge 80 to filter or smooth out the cyclical DC output from the rectifier bridge to supply a substantially constant voltage source to regulator U6. Supply circuit 47 also utilizes a capacitor C11, connected across output pin 92 and ground pin 94 of regulator U6 to minimize drifting of the regulator, especially when the regulator is operating in a no load condition. As a consequence, regulator U6 is capable of producing a substantially constant output voltage at all times.

The DC output signal from regulator U6 is transmitted through a rail voltage line 98, through resistor R24 and through connector 612 to an indicator lamp CR10 which is energized whenever switch S1 is closed thereby informing the operator that apparatus 10 has been turned on. Preferably lamp CR10 is of a type which requires very little current to operate, such as a light emitting diode type of lamp. The opposite side of lamp CR10 is connected to a circuit common line 96 originating from voltage regulator U6.

The operating cycle of apparatus 10 is initiated by closure of a momentary contact, cycle start switch S3 which causes a high-level signal to be transmitted through connector 603 to the gate of a thyrister Q4, turning it on. The thyrister Q4 produces a high-level signal which is applied to reset terminal 504 of a monolithic, linear integrated timer circuit or unit U5 of dwell circuit 40 thereby terminating the low-level reset signal to the dwell circuit which originated when switch S1 was initially closed. Preferably switch S3 is biased by a spring or other means to remain open other than when the switch is momentarily closed to initiate the operating cycle of apparatus 10. The momentary closing of cycle start switch S3 also causes a low voltage signal to be applied to trigger pin 502 of timing unit U5. Switch S3 is interconnected with ground line 96 by connector 601.

Unit U5 is wired as a time delay unit and includes a ground pin 501 connected to ground line 96 and an input pin 508 connected to common rail 98. When the low voltage signal caused by the closing of switch S3 is applied to trigger pin 502 of timing unit U5, a transistor, not shown, which connects a discharge pin 507 to ground, is switched off thereby initiating the charging of a capacitor C10 which is connected to common rail 98 through variable resistor R5 and resistor R6. The charge level in capacitor C10 is sensed by the threshold pin 506 of U5 so that when the charge level in C10 reaches two-thirds of the rail voltage applied at pin 508, the transistor, not shown, connected to pin 507 is switched to ground thereby rapidly discharging capacitor C10. The rate at which capacitor C10 is charged determines the delay or dwell period between the time that start switch S3 is closed and the time lamp 12 is switched to its high or operating level, which dwell period is dependent on the sum of the resistances of resistors R16 and R5. This dwell time length may be altered by varying the resistance of variable resistor R5.

The trigger pin 502 of U5 is tied to rail line 98 through a very large resistor R4. This prevents timing unit U5 from being accidently triggered by transients occurring in rail line 98 originating from, for instance, the turning on of a heavy piece of equipment located nearby apparatus 10. In effect, resistor R4 serves as a buffer to insure that timing unit U5 is definitely in either a triggered or untriggered state.

The voltage control pin 505 of timing unit U5 is tied to ground through capacitor C9. This capacitor, which is charged by an internal connection between pins 505 and 508, serves as a constant reference voltage for timing unit U5 to insure that the timing unit functions properly.

When capacitor C10 discharges through pin 507 to one-third of the level of the rail voltage at pin 508, a low-level signal is produced at output pin 503 of timing unit U5. This low-level signal is transmitted to triggering pin 402 of a timing unit U4 of operating cycle control circuit 42 through capacitor C7 thereby initiating the switching of lamp 12 to its high-level or operating state. As discussed above relative to timing unit U5, the low-level reset signal imposed on pin 404 has been released by a high-level signal applied to the reset pin from the output of thyrister Q4. The application of the low-level triggering signal to pin 402 causes timing unit U4 to produce a high-level signal at output pin 403 which is transmitted to the base of a transistor Q3 through resistor R18. The emitter of transistor Q3, which is interconnected with the output pin 503 of timing unit U5, receives the same low-level signal which is applied to triggering pin 402 of timing unit U4. The application of a high-level signal to the base and a low-level signal to the emitter of transistor Q3 turns it on causing it to output a low-level signal from its collector, which signal is transmitted to one side of coil 614 of relay K1 of switching circuit 38 thereby energizing the relay. The opposite side of coil 614 is connected to rail voltage line 98. As discussed more fully below, the energizing of relay K1 causes it to switch transformer T1 to in turn energize lamp 12 to its high intensity level. A commutating diode CR8 is connected across coil 614 to "absorb" the reverse flow current which is generated in the coil by the collapse of the field around the coil when the coil is deenergized by the termination of the high output from transistor Q3. By using diode CR8 to route this reverse polarity current back through coil 614 rather than allowing the current to reach other portions of apparatus 10, potential blowout of other components is eliminated.

The duration of the high-level control signal produced at output pin 403 of timing unit U4 may be selectively altered by adjustment of time select switch 44. When the low-level signal from pin 503 of timing unit U5 is applied to triggering pin 402 of timing unit U4, an internal transistor, not shown, connected to discharge pin 407 is switched from ground to off thereby initiating the charging of capacitor C8 by current from rail voltage line 98 which first passes through time select switch 44. Time select switch 44 is composed of a plurality of resistors R6–R11 which may be selectively interconnected with each other by rotating a thumb wheel 616 thereby altering the effective impedance of the selector switch which in turn varies the rate at which capacitor C8 charges up.

Threshold pin 406 of timing unit U4 senses the charge level in capacitor C8. Once the charge level reaches two-thirds of the rail voltage at input pin 408, the transistor, not shown, connected to discharge pin 407, is switched to ground to discharge capacitor C8 and thereby switching the output at discharge pin 403 to a low-level which in turn causes transistor Q3 to turn off. When transistor Q3 turns off, coil 614 of relay K1 is deenergized which switches transformer T1 back to its low output level to return lamp 12 back to its low intensity state.

In a preferred form of the present invention, thumb wheel 616 may be rotated into six different positions which in turn interconnects resistors R6-R11 in six different combinations thereby causing timing unit U4 to produce a control signal at pin 403 for from ten to sixty seconds in ten-second intervals. It is to be understood, however, that intervals of other lengths of time may be used. Also, time select switch 44 may be replaced by other types of switches, such as those which are infinitely variable from between zero to a maximum number of seconds.

The control voltage pin 405 of timing unit U4 is connected to a variable resistance resistor R14. One side of resistor R14 is connected to ground line 96 and the opposite side is connected to input pin 408 which in turn is connected to rail voltage line 98. The effective impedance of resistor R14 may be adjusted to compensate for tolerance variations in the components of operating cycle control circuitry 42 and selector switch 44 and the other components of apparatus 10 so that timing unit U4 produces a control signal at pin 403 for precisely the desired length of time.

In a manner similar to timing unit U5, trigger pin 402 of timing unit U4 is connected to rail voltage line 98 through high a impedance resistor R3. Resistor R3 functions similarly to R4 to prevent accidental triggering of timing unit U4 by transients occurring in rail voltage line 98.

As discussed above, unless a control signal is produced by operating cycle control circuit 42, when switch S1 is closed, lamp 12 is maintained at a low or preheat level. However, when a control signal is outputted at pin 403 of timing unit U4, relay coil 614 is energized thereby pivoting blade 72 to open contacts 69 and 70 and close contacts 70 and 71 as schematically illustrated in broken line in FIG. 3. When this occurs, lamp 12 is subjected to the full output voltage of transformer T1. Rather than fully energizing lamp 12 exactly when contacts 70 and 71 are closed, switching circuitry 38 coordinates the energizing of lamp 12 to take place when the AC supplied by transformer T1 is passing through a zero voltage level.

When relay K1 is deenergized and lamp 12 is in its low output mode, switching circuit 38 is also in a standby mode with current from transformer T1 flowing through a resistor R22 and a triac Q1 wired in series across both secondary coils of the transformer. When the current across pins M1a and M2a of triac Q1 is either positively or negatively rising, current flows out of gate 619 to charge capacitor C13 thereby producing enough of a relative voltage difference between the gate and pin M1a to permit current to flow through triac Q1. When the current is in its decreasing voltage phase, capacitor C13 discharges through R21 so that by the time zero voltage is reached, capacitor C13 is fully discharged and ready to be charged in an opposite polarity from the previous charge.

When relay K1 is energized, terminals 69 and 70 are open while terminals 70 and 71 are closed thereby shorting out gate 619 of triac Q1 with pin M2a so that with the next change in direction of the alternating current from transformer T1, triac Q1 is switched off thereby preventing current from passing therethrough. Simultaneously, triac Q2 becomes operational causing the full output of transformer T1 to be imposed across lamp 12. Triac Q2 is also connected across both coils of transformer T1 with pin M1b of the triac connected to the far side of transformer coil 54 and pin M2b of the triac connected to the far side of coil 52 through lamp 12. A resistor R23 is connected between pin M2b of triac Q2 and its gate 620 so that enough of a potential difference exists between the gate and pin M2b to allow the AC to flow through the triac when the voltage at pin M1b of triac Q2 is negative. Current flows across resistor R23 from terminal 621 to terminal 622 drawing current out from gate 620 to terminal 621. Correspondingly, when the AC at terminal M1b of triac Q2 is positive, current flows across resistor R23 from terminal 622 to terminal 621 and into gate 620.

Switching circuit 38 also includes rectifier diodes CR5 and CR6 which are connected in parallel between pin M1 of triac Q1 and gate 620 of triac Q2. When triac Q1 is activated and triac Q2 is deactivated, i.e. during the standby state of switching circuit 38, the inherent impedances of rectifier diodes CR5 and CR6 prevent current flowing across triac Q1 from reaching the gate of triac Q2, thereby preventing Q2 from being activated.

It will be appreciated that by the above-described construction of switching circuit 38, although the cycle control circuit produces a control signal which activates relay K1 to thereby switch lamp 12 to its full output state, the full output of transformer T1 is not imposed across lamp 12 until the voltage of the AC is at zero. This eliminates the possibility that a high current level is suddenly imposed across the filament of lamp 12, which filament when cold has very little impedance. If the entire maximum voltage output of transformer T1 were suddenly applied across the cold filament of lamp 12, an effective short circuit would result which could cause damage to the lamp. By switching the full output of transformer T1 when the AC is at zero voltage, the current level through the filament of lamp 12 is allowed to gradually increase as the filament warms up. As a result, applicants' have found that the service life of lamp 12 is several times longer than if zero voltage switching were not used.

The present invention also includes a tone generating circuit 98 which produces an audible signal when lamp 12 is initially switched to its full on condition and then subsequently generates an audible signal at periodic intervals during the duration that the lamp is fully energized. As discussed above relative to the operation of transformer K1, transistor Q3 produces a low-level output signal at its collector when it receives a low-level signal at its emitter from timing unit U5 and a high-level signal at its base from timing unit U4. The low-level signal from transistor Q3 is transmitted to ground pin 101 of a timing unit U1 of tone generating circuit 98. Even prior to the starting of an operating cycle by closure of switch 3, when switch 1 is initially closed, capacitor C2, connected between ground line 96 and voltage rail line 98 through variable resistor R1, immediately begins charging up. Capacitor C2 is able to accumulate a charge because until timing unit U1 receives a low-level signal at its ground pin 101, it is inactivated. Since by the time cycle start switch S3 is closed capacitor C2 has already been fully charged, when timing unit U1 receives a low-level signal at its ground pin 101, capacitor C2 immediately discharges to ground through a transistor, not shown, connected to discharge pin 107. The discharge of capacitor C2 is sensed by threshold pin 106 thereby immediately causing timing unit U1 to produce a low-level short duration pulse at output pin 103, which pulse is transmitted to the triggering pin 202 of another timing unit U2. Discharge pin 107 and triggering pin 102 of timing unit U1 are wired together so that when capacitor C2 discharges to ground, the resulting low-level signal at discharge pin 107 is transmitted to triggering pin 102 to retrigger the timing unit U1. Thus, since reset pin 104 is tied to rail voltage line 98, the timing unit is automatically reset after each time capacitor C2 discharges to one-third of the voltage level at voltage input pin 108. Capacitor C2 immediately begins to charge up again by receiving current from rail line 98 through variable resistor R1. The effect of impedance of resistor R1 may be selectively altered to vary the cycling time of timing unit U1 to thereby produce a short low-level pulse at output pin 103 at desired intervals, for instance in ten-second intervals.

The low-level output pulse transmitted to triggering pin 202 of timing unit U2 from output pin 103 of timing unit U1 causes timing unit U2 to initially produce a high-level output signal at output pin 203. Previously the high output signal from thyrister Q4 produced by the closing of switch S3 had been routed to pin 204 of timing unit U2 to release the low-level reset signal produced by the closing of switch S1. The high-level output signal from pin 203 of timing unit U2 is transmitted to reset pin 304 and voltage input pin 308 of a further timing unit U3 and to indicator lamp CR9 through resistor R19 causing the lamp to flash for the duration of the high output signal. The opposite side of lamp CR9 is tied to ground line 96 through connector 601. Preferably lamp CR9 is of a type which requires, very little current for its operation, such as a light emitting diode type.

As with timing units U4 and U5, ground pin 201 of timing unit U2 is tied to ground line 96, and voltage input pin 208 is tied to rail line 98. Upon receipt of the low-level pulse at triggering pin 202 of timing unit U2, capacitor C4, tied between ground line 96 and rail line 98 through resistor R12, begins to accumulate a charge. When the charge level in capacitor C4 reaches two-thirds of the voltage at pin 208, a transistor, not shown, connected to discharge pin 207, is switched to ground thereby rapidly discharging capacitor C4 until the charge in the capacitor drops down to one-third of the voltage level at pin 208. When this occurs, timing unit U2 is internally switched so that a low output signal is produced at output pin 203. Resistor R12 and capacitor C4 are sized so that it takes approximately one second for capacitor C4 to charge up and discharge upon the triggering of timing unit U2. As a consequence, the high output signal at output pin 203 lasts for approximately one second. After capacitor C4 has discharged, it does not immediately begin recharging since the low output pulse at triggering pin 202 has already terminated and has been replaced by a high-level signal.

The high-level signal applied to pin 304 of timing unit U3 from output pin 203 of timing unit U2 releases the previous low-level reset signal applied to pin 304 by timing unit U2. Imposition of this same high-level signal to voltage input pin 308 of timing unit U3 causes the timing unit to initially produce a high-level output signal at output pin 303 which is transmitted to piezoelectric transducer DS1 through variable resistor R17. Triggering pin 302 of timing unit U3 is tied directly to threshold pin 306 and to discharge pin 307 through resistor R13. Thus, when output pin 203 of timing unit U2 produces a high-level output signal, capacitor C6 immediately begins charging through resistors R13 and R2. When the charge level in capacitor C6 reaches two-thirds of the voltage level at pin 308, as sensed by threshold pin 306, a transistor, not shown, connected to discharge pin 307, is switched to ground thereby discharging capacitor C6. When threshold pin 306 senses that capacitor C6 has discharged down to one-third of the voltage level at pin 308, timing unit U3 is switched to discharge a low-level signal at output pin 303 thereby terminating the signal to transducer DS1. Resistors R2 and R13 and capacitor C6 are sized to switch timing unit U3 very rapidly, for instance at a frequency of 4,000 hertz thereby driving transducer DS1 to produce an audible signal. The volume of the audible signal may be controlled by varying the effective impedance across the variable resistor R17. Since voltage input pin 308 of timing unit U3 is tied to output pin 203 of timing unit U2, transducer DS1 generates an audible signal only for the length of time that timing unit U2 produces a high-level output signal, preferably for about one second. The first audible signal produced by transducer DS1 notifies the operator that lamp 12 has been switched to its high output level and then each subsequent signal indicates that a time interval during which the lamp is at its high output level has elapsed.

When the voltage at threshold pin 406 of timing unit U4 rises to two-thirds of the rail voltage level at input pin 408 due to the charging of capacitor C8, the capacitor discharges through pin 407 which causes the output at pin 403 to switch to a low-level which, in turn, turns off transistor Q3. When transistor Q3 is thus locked out, it causes transformer K1 and timing units U1, U2 and U3 to shut down thereby deenergizing lamp 12 and preventing any further audible signal to be produced. The above-described operating cycle of apparatus 10 may be repeated by again momentarily closing operating cycle start switch S3, with the length of the operating cycle controlled by the adjustment of time select switch 44.

Typical components composing light generating apparatus 10, as discussed above, are listed below on Table 1.

As will be apparent to those skilled in the art to which the invention is addressed, the present invention may be embodied in forms other than that specifically disclosed above without departing from the spirit or essential characteristics of the invention. The particular embodiment of the light generating apparatus 10, as described above, is therefore to be considered in all respects as illustrative and not restrictive, with the scope of the present invention being set forth in the appended claims, rather than being limited to the foregoing description.

TABLE 1

| TYPICAL COMPONENTS | |
| --- | --- |
| Reference Designation | Description |
| C1 | .01 $\mu f$ |
| C2 | 100 $\mu f$ |
| C3 | .01 $\mu f$ |

TABLE 1-continued
TYPICAL COMPONENTS

| Reference Designation | Description |
|---|---|
| C4 | 100 μf |
| C5 | .01 μf |
| C6 | .1 μf |
| C7 | .01 μf |
| C8 | 100 μf |
| C9 | .01 μf |
| C10 | 100 μf |
| C11 | .1 μf |
| C12 | 220 μf |
| C13 | .1 μf |
| C14 | .10 μf |
| CR1 | 1N4004 |
| CR2 | 1N4004 |
| CR3 | 1N4004 |
| CR4 | 1N4004 |
| CR5 | 1N4004 |
| CR6 | 1N4004 |
| CR8 | 1N4004 |
| CR9 | Z106 |
| CR10 | Z102 |
| CR11 | 1N5239 |
| DS1 | EFB-RD-24C01 |
| K1 | 49RE1C1 |
| Q1 | Q200E3 |
| Q2 | Q4015L5 |
| Q3 | 2N2924 |
| Q4 | 2N5060 |
| R1 | 250K ohm, ½ Watt, 5% |
| R2 | 1K ohm, ½ Watt, 5% |
| R3 | 22M ohm, ½ Watt, 5% |
| R4 | 1M ohm, ½ Watt, 5% |
| R5 | 100K ohm, ½ Watt, 5% |
| R6 | 100K ohm, ½ Watt, 5% |
| R7 | 100K ohm, ½ Watt, 5% |
| R8 | 100K ohm, ½ Watt, 5% |
| R9 | 100K ohm, ½ Watt, 5% |
| R10 | 100K ohm, ½ Watt, 5% |
| R11 | 100K ohm, ½ Watt, 5% |
| R12 | 4.7K ohm, ½ Watt, 5% |
| R13 | 1.6K ohm, ½ Watt, 5% |
| R14 | 100K ohm, ½ Watt, 5% |
| R15 | 1K ohm, ½ Watt, 5% |
| R16 | 100K ohm, ½ Watt, 5% |
| R17 | 10K ohm, ½ Watt, 5% |
| R18 | 150 ohm, ½ Watt, 5% |
| R19 | 330 ohm, ½ Watt, 5% |
| R20 | 2K ohm, ½ Watt, 5% |
| R21 | 330 ohm, ½ Watt, 5% |
| R22 | 150 ohm, 2 Watt, 5% |
| R23 | 51 ohm, 1 Watt, 5% |
| R24 | 330 ohm, ½ Watt, 5% |
| RV1 | V24ZA4 |
| U1 | NE555 |
| U2 | NE555 |
| U3 | NE555 |
| U4 | NE555 |
| U5 | NE555 |
| U6 | UA7812 |

We claim:

1. An apparatus for interconnecting an alternating current source with light generating means for a time cycle beginning after an initial dwell time, comprising:
    (a) time delay means;
    (b) cycle control means operatively coupled to said time delay means, said cycle control means being activated for a preselected time interval after activation of said time delay means; and
    (c) switch means coupled with said cycle control means and interconnected between the alternating current source and the light generating means, said switch means:
    in response to the activation of said cycle control means, interconnecting the alternating current source with the light generating means when the alternating current source crosses a zero voltage point in the alternating current cycle; and
    in response to the deactivation of said cycle control means, disconnecting the alternating current source from the light generating means.

2. The apparatus according to claim 1, wherein said time delay means produces an output signal at a preselected time period after activation of said time delay means.

3. The apparatus according to claim 2, wherein said cycle control means produces a control signal for a fixed time interval in response to said output signal.

4. The apparatus according to claim 3, wherein said switch means:
    upon production of said control signal, interconnects the alternating current source with the light generating means when the alternating current source crosses a zero voltage point in the alternating current cycle; and
    upon termination of said control signal, disconnects the alternating current source from the light generating means.

5. The apparatus according to claim 3 or 4, wherein said cycle control means includes selectively adjustable means for producing said control signal for a variable time interval.

6. The apparatus according to claim 4, wherein:
    the alternating current source produces a low-level energy output and a high-level energy output; and
    said switching means nominally interconnects the light generating means with the low-level output of the alternating current source and upon production of said control signal, interconnects the light generating means with the high-level output of the alternating current source.

7. The apparatus according to claim 6, wherein said switching means upon production of said control signal maintains the interconnection of said light generating means with the low-level alternating current output until the alternating current source crosses a zero voltage point in the alternating current cycle thereupon switching said light generating means to said high-level output.

8. The apparatus according to claim 4, further comprising tone generating means operably coupled with said cycle control means for periodically producing an audible signal during the duration of said control signal.

9. The apparatus according to claim 8, wherein said tone generating means produces said audible signal at the end of each time interval elapsing during the duration of said control signal.

10. The apparatus according to claim 1, wherein:
    said cycle control means producing a control signal for a selectively adjustable time interval; and
    said switch means:
    upon production of said control signal, interconnects the alternating current source with the light generating means when said alternating current source crosses a zero voltage point in the alternating current cycle; and in response to the termination of said control signal, disconnects the alternating current source from the light generating means.

11. The apparatus according to claim 10, wherein:
    the alternating current source produces a low-level energy output and a high-level energy output; and
    said switching means nominally interconnects the light generating means with the low-level output of the alternating current source and upon production of said control signal, interconnects the light generating means with the high-level output of the alternating current source.

12. The apparatus according to claim 10, further comprising tone generating means operably coupled with said cycle control means for periodically producing an audible signal during the duration of said control signal.

13. The apparatus according to claim 1, wherein:
the alternating current source produces a low-level energy output and a high-level energy output; and
said switching means nominally interconnects the light generating means with the low-level output of the alternating current source and in a response to the activation of said cycle control means, interconnects the light generating means with the high-level output of the alterating current source.

14. The apparatus according to claim 1, further comprising tone generating means operably coupled with said cycle control means for periodically producing an audible signal during activation of said cycle control means.

15. The apparatus according to claim 14, wherein said tone generating means produces an audible signal when said cycle control means is first activated and then at the end of each time interval lapsing during activation of said cycle control means.

16. The apparatus according to claim 1, wherein said light generating means includes a quartz halogen lamp.

17. The apparatus according to claim 1, further comprising fan means for circulating cooling air over said apparatus.

18. An apparatus for photochemically curing organic composites used to repair teeth, comprising:
(a) light generating means;
(b) means for applying the light produced by said light generating means on the organic composites;
(c) time delay means for producing an output signal at a preselected time period after activation of said time delay means;
(d) cycle control means operably coupled to said time delay means to produce a control signal for a preselected time interval in response to said output signal; and
(e) switch means coupled with said cycle control means and interconnected between an alternating current source and said light generating means, said switch means:
in response to said control signal, interconnecting the alternating current source with said light generating means at the point in the alternating current cycle when the alternating current crosses a zero voltage level; and
upon termination of said control signal, disconnecting the alternating current source from said light generating means.

19. The apparatus according to claim 18, wherein said cycle control means includes adjustable means for producing said control signal for a selective time interval.

20. The apparatus according to claim 18:
further including means for transforming the alternating current either to a low-level output voltage, or to a high-level output voltage; and
wherein said switching means interconnects said light generating means alternatively with said low-level output voltage in the absence of said control signal, or with said high-level output voltage in the presence of said control signal.

21. The apparatus according to claim 20, wherein said switching means upon receipt of said control signal switches said light generating means from said low-level voltage output to said high-level voltage output when the alternating current crosses a zero voltage point in the alternating current cycle.

22. The apparatus according to claim 18, further including tone generating means operably coupled with said cycle control means for producing an audible signal at the beginning of said control signal and then periodically at fixed time intervals during the duration of said control signal.

* * * * *